US008751012B2

(12) United States Patent
Jäger et al.

(10) Patent No.: US 8,751,012 B2
(45) Date of Patent: Jun. 10, 2014

(54) IMPLANTABLE VESTIBULAR PROSTHESIS SYSTEM WITH POWER SAVING MODE INCLUDING SOFT START AND SOFT POWER-DOWN

(71) Applicant: MED-EL Elektromedizinische Geraete GmbH, Innsbruck (AT)

(72) Inventors: Andreas Jäger, Reith bei Seefeld (AT); Carolyn Garnham, Matlock Derbyshire (GB); Roland Hessler, Innsbruck (AT); Martin Zimmerling, Patsch (AT); Charles Coleman Della Santina, Towson, MD (US); Gene Fridman, Santa Clarita, CA (US)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/743,513

(22) Filed: Jan. 17, 2013

(65) Prior Publication Data

US 2013/0184788 A1 Jul. 18, 2013

Related U.S. Application Data

(60) Provisional application No. 61/587,251, filed on Jan. 17, 2012.

(51) Int. Cl.
*A61N 1/00* (2006.01)
(52) U.S. Cl.
USPC .......................................................... 607/62
(58) Field of Classification Search
USPC .......................................................... 607/62
See application file for complete search history.

(56) References Cited

U.S. PATENT DOCUMENTS

| 4,769,881 A | 9/1988 | Pedigo et al. ............. 128/419 R |
| 6,314,324 B1 * | 11/2001 | Lattner et al. .................. 607/42 |
| 7,925,350 B1 | 4/2011 | Palmer ............................ 607/32 |
| 2007/0208403 A1 | 9/2007 | Della Santina et al. ....... 607/137 |
| 2008/0208284 A1 | 8/2008 | Rezai et al. ..................... 607/45 |
| 2009/0082831 A1 | 3/2009 | Paul et al. ........................ 607/59 |
| 2009/0264967 A1 | 10/2009 | Giftakis et al. ................. 607/62 |

FOREIGN PATENT DOCUMENTS

| WO | 2011/088130 A2 | 7/2011 | |
| WO | 2011/161562 A1 | 12/2011 | ............... A61N 1/36 |

OTHER PUBLICATIONS

U.S. Patent and Trademark Office, Officer Lee W. Young, International Search Report and Written Opinion, PCT/US13/21820, date of mailing Mar. 29, 2013, 12 pages.

* cited by examiner

*Primary Examiner* — George Manuel
(74) *Attorney, Agent, or Firm* — Sunstein Kann Murphy & Timbers LLP

(57) ABSTRACT

A novel vestibular implant system is described. An implantable vestibular stimulator provides vestibular stimulation signals to stimulate target neural tissue for vestibular sensation by a patient. One or more motion sensors are controllably powered by the vestibular implant system and develop a motion signal reflecting head motion of an implant patient. The vestibular stimulator includes at least two different operating modes: i. a sensor controlled mode wherein the motion sensor is powered and the vestibular stimulation signal is developed as a dependent function of the motion signal, and ii. a sensor independent mode wherein the motion sensor is unpowered and the vestibular stimulation signals, if any, are developed independently of the motion signal.

19 Claims, 2 Drawing Sheets

IMPLANTABLE VESTIBULAR PROSTHESIS SYSTEM WITH POWER SAVING MODE INCLUDING SOFT START AND SOFT POWER-DOWN

This application claims priority from U.S. Provisional Patent Application 61/587,251, filed Jan. 17, 2012, which incorporated herein by reference.

TECHNICAL FIELD

The present invention relates to implantable stimulation systems, and more specifically to a vestibular implant system with a power management functionality.

BACKGROUND ART

A normal ear directs sounds as shown in FIG. 1 from the outer ear pinna 101 through the generally cylindrical ear canal 110 to vibrate the tympanic membrane 102 (eardrum). The tympanic membrane 102 moves the bones of the middle ear 103 (malleus, incus, and stapes) that vibrate the cochlea 104, which in turn functions as a transducer to generate electric pulses to the brain that are interpreted as sounds.

In addition, the inner ear also includes a balance sensing vestibular system which involves the vestibular labyrinth, its three interconnected and mutually orthogonal semi-circular canals: the superior canal 106, posterior canal 107, and horizontal canal 108 (as well as the otolith organs 116 in the utricle and saccule of the inner ear. The canals and otoliths of the vestibular labyrinth contain hair cells 118 in a viscous endolymph 117 to sense head orientation and head movements, thereby activating vestibular nerve fibers 119 that send an electrical balance signal to the brain 105.

In some people, the vestibular system is damaged or impaired. Such vestibular dysfunction can cause balance problems such as unsteadiness, vertigo and unsteady vision. This can be a significant handicap in everyday life. To treat such problems, stimulation of the vestibular system can help to restore the balancing function, and vestibular implants are currently under development to provide such an artificial balance signal.

FIG. 1 also shows some components of a vestibular implant system such as is described in U.S. patent application Ser. No. 61/366,345 (incorporated herein by reference). An external movement signal (from one or more sensors not shown) is processed by an external processor 111 to produce a vestibular stimulation signal. An external transmitter coil 112 couples the stimulation signal through the skin to an implanted receiver coil 113. Implanted vestibular stimulator 114 than delivers the stimulation signal through an electrode lead 109 to vestibular stimulator electrodes 115 that stimulate target neural tissue such as the semicircular canals 106, 107, 108, one or both otolith organs, and/or the vestibular nerve 105 or ganglion for vestibular sensation by the patient as a balance signal.

In animal evaluations of vestibular implant systems, stimulation modulation appears to be effective where the stimulus strength is rate-modulated around a baseline rate and/or amplitude-modulated according to rotational acceleration. But a human patient may experience discomfort (vertigo, etc.) when such an implant initially is powered up and starts to stimulate, as well as when ongoing stimulation stops. It is therefore desirable for the implant power supply to provide stimulation energy that is if possible uninterrupted at all times.

In addition, existing gyro sensors used in vestibular implant systems have relatively high power consumption and require a relatively large battery (either in the implanted part or in an external part of the vestibular implant system) and/or relatively frequent battery re-charging cycles. But again the onset of stimulation (when the vestibular implant is being activated) and switching off (e.g. when the battery is depleted) will be required from time to time, which are challenging situations as the respective changes in stimulation patterns can result in severe discomfort (vertigo etc.). Additionally, in certain situations such a change or loss of stimulation patterns can be possibly dangerous, especially when occurring unexpectedly.

SUMMARY

Embodiments of the present invention are directed to a vestibular implant system in which an implantable vestibular stimulator provides vestibular stimulation signals to stimulate target neural tissue for vestibular sensation by a patient. One or more motion sensors are controllably powered by the vestibular implant system and develop a motion signal reflecting head motion of an implant patient. The vestibular stimulator includes at least two different operating modes: i. a sensor controlled mode wherein the motion sensors and other electronic components of the stimulator are powered and the vestibular stimulation signals are developed as a dependent function of the motion signal, and ii. a sensor independent mode wherein the motion sensors and possibly some other electronic components of the stimulator are unpowered and the vestibular stimulation signals, if any, are developed independently of the motion signal.

The system may further include at least one mode control sensor separate and independent from the at least one motion sensor which develops a mode control signal reflecting head motion of the implant patient. From that, the vestibular stimulator system shifts to sensor independent mode when then mode control signal falls below a threshold value. For example, the system may shift to sensor controlled mode when the mode control signal exceeds the threshold value. Or the vestibular stimulator system may shift to sensor independent mode when the motion signal falls below a threshold value. And again the system may shift to sensor controlled mode when the motion signal exceeds the threshold value.

The vestibular stimulation signal may be a constant pacing signal in sensor independent mode, or there may be no vestibular stimulation signal developed in sensor independent mode. The system may shift operating modes as a function of time of day, in response to a system malfunction, or as a function of system power status. The sensor independent mode may include a patient sleep mode so that the vestibular stimulation signal is adapted to promote sleep of the patient or any other situation in which the patient does not need or want to receive stimulation.

Embodiments of the present invention also include a vestibular implant system having an implantable vestibular stimulator that provides a vestibular stimulation signal to stimulate target neural tissue for vestibular sensation by a patient, and one or more motion sensors that develop a motion signal reflecting head motion of an implant patient. The vestibular stimulator includes at least two different operating modes: i. a sensor controlled mode wherein the vestibular stimulation signals are developed as a dependent function of the motion signal, and ii. a power shifting mode wherein the vestibular stimulation signals are adapted to change over time to reduce patient discomfort while changing power operation of the system.

The system may be operated in power shifting mode when starting up and/or when shutting down. Adaptation of the vestibular stimulation signal may include changing over time the pulse duration, pulse repetition rate, pulse train length, and/or signal amplitude.

The system may further include one or more physiologic sensors that develop a physiologic signal reflecting a physiological condition of an implant patient. From that, adaptation of the vestibular stimulation signal may further be responsive to the physiological signal.

DETAILED DESCRIPTION

One aspect of the present invention is based on having different operating modes of the vestibular implant system with sensors and/or other parts of the implant's electronics being used in an adaptive way. Such an adaptation is beneficial to save electrical power, to extend battery time until recharging is needed and to increase battery life time while maintaining essential device functions.

Figure 1:
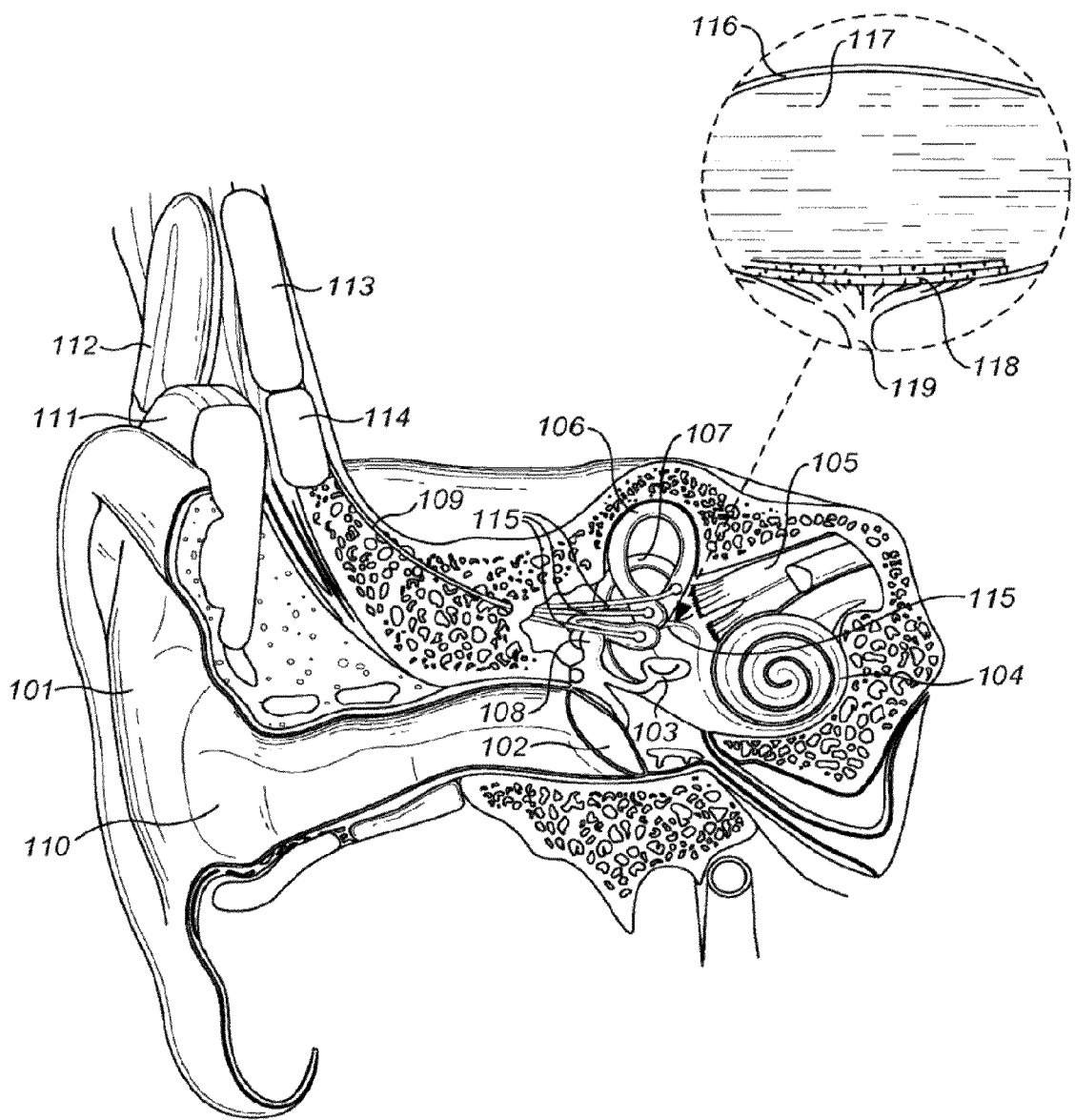
FIG. 1 shows various anatomical structures in a human ear including one specific embodiment of a vestibular implant system.

Take, for example, a vestibular implant such as the one shown in FIG. 1 where the implanted vestibular stimulator 114 or the external processor 111 house and controllably power one or more motion sensors that develop a motion signal reflecting head motion of the patient. For example, such a motion sensor may be located either within the housings of the implanted stimulator 114 or the external processor 111, or it may be separate from their housings and connected to one of them by a connecting lead. According to an embodiment of the invention, then, the implanted stimulator 114 includes at least two different operating modes as illustrated by the state diagram shown in FIG. 2 where the two operating modes are ON and STANDBY. ON is a sensor controlled mode wherein the motion sensors and other electronic components of the stimulator are powered and the vestibular stimulation signals are developed as a dependent function of the motion signal. STANDBY is a sensor independent mode wherein the motion sensors and/or other electronic components of the stimulator are unpowered and the vestibular stimulation signal, if any, is developed independently of the motion signal.

When the system shifts from sensor controlled ON mode to sensor independent STANDBY mode, power is removed from sensors and/or other components deactivating them, thereby conserving limited power resources. For example, this may occur in response to the processor in the implanted stimulator 114 detecting that the rotational acceleration of the motion sensors falls below some threshold value. Or in some embodiments, there may also be one or more mode control sensors that operate separately of and independently from the motion sensors to develop a "watchdog" mode control signal reflecting head motion of the implant patient. For example, the mode control sensor may be a linear accelerometer sensor which requires less power than the gyro based motion sensor. Then when the mode control signal falls below a threshold value the system shifts from rotational sensor controlled ON mode to rotational sensor independent STANDBY mode, power is removed from sensors and/or other components deactivating them, thereby conserving limited power resources. The linear accelerometers may be operated in an adaptive mode with reduced power consumption when the linear accelerations remain below a certain threshold value. Once sufficient power resources are available again (e.g., the battery has recharged) and the motion signal or the mode control signal exceeds the threshold value, then the system may re-power the motion sensor and shift back to sensor controlled mode ON.

Power is further conserved in sensor independent STANDBY mode by adapting the stimulus signal, if any, consistent with the now unpowered motion sensors and the corresponding loss of the motion signal input. In some embodiments, under some circumstances, this will mean that the implant simply does not provide any stimulation at all to the patient's vestibular system. For example, this may occur when the battery is empty or switched off (In the case of a semi-implantable vestibular implant system with external battery this can also happen when the link is lost between the external component and the implantable component.) The power-saving sensor independent STANDBY mode also may include circumstances where rotational and linear motion sensors are switched off sequentially and even individually for all three axes, i.e. starting with deactivation of sensor(s) of a first and then a second axis before also the sensor(s) for the third (most important) axis is being switched off. Also device components which are auxiliary to sensor function may be switched off.

Figure 2:
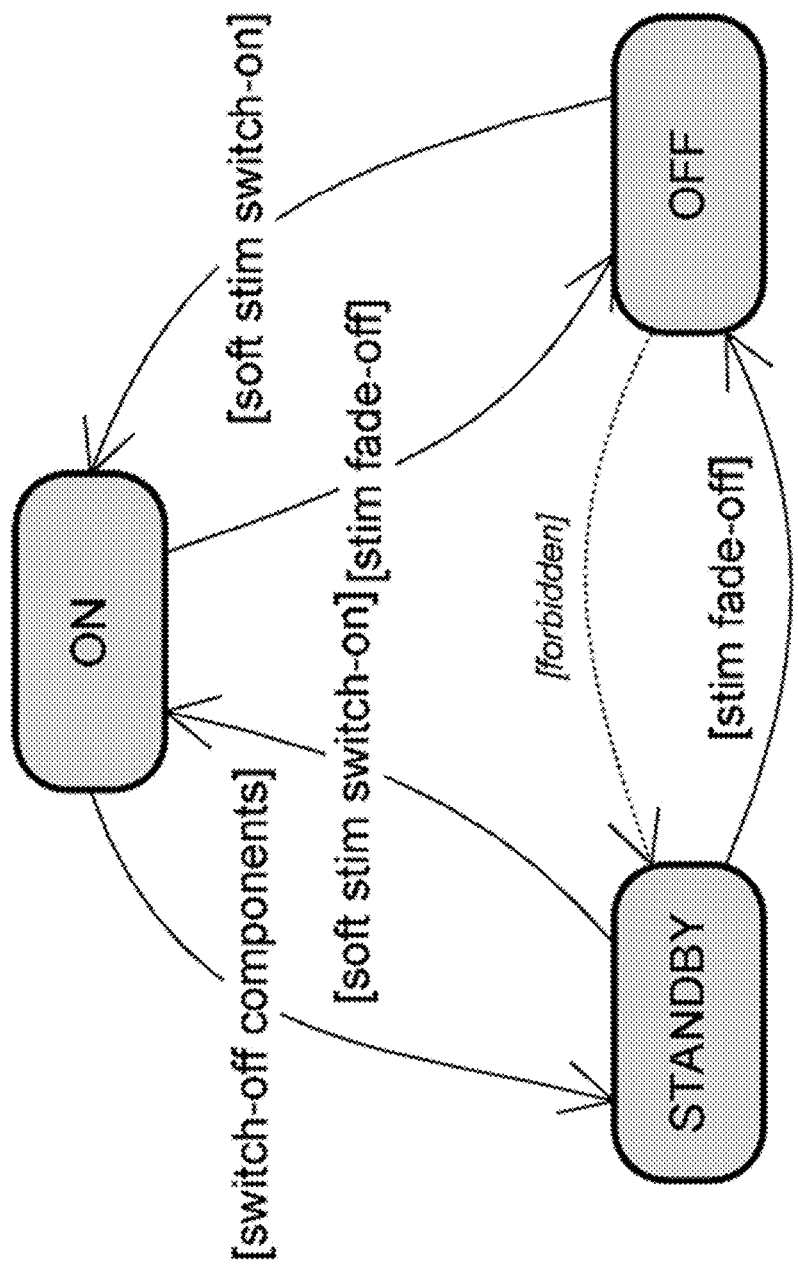
FIG. 2 shows a state diagram of a vestibular implant system according to an embodiment of the present invention.

FIG. 2 also shows that when switching the system to the sensor controlled ON mode a soft start switch-on process may be useful. Similarly, when switching the system to the OFF state, there may be a soft-off power down. Over a period of time during the soft-start and soft-off, the patterns of the stimulation signals are gradually transitioned to minimize discomfort for the patient. For example, the stimulation intensity (pulse duration and/or pulse amplitude) gradually increased or decreased (for soft-start and soft-off power-down respectively) over a certain period of time. Or for soft-start the pattern of the stimulation signal may start with shorter pulse trains (constant amplitude, constant pulse rate) with relatively long gaps between those pulse trains. Then the pulse trains slowly become longer while at the same time the gaps between these pulse trains are fading until a continuous stimulation is obtained. The same principle can be applied for soft-power-down where pulse gaps are included. (Note: As rotational information is mainly encoded in stimulation rate, it is desired to be kept constant during the soft-start and soft-off.)

The system may shift operating modes as a function of time of day, in response to a system malfunction, or as a function of system power status. The sensor independent mode may include a patient sleep mode so that the vestibular stimulations signal are adapted to promote sleep of the patient. In such a constant pacing mode, motion-dependent modulation of stimulation is not needed. Mode shifting and adaptation of the stimulation signal may further be based on and reflect one or more physiologic signal inputs to further minimize unpleasant sensations (e.g. seen by nystagmus) for the patient. Besides control by the system itself, mode shifting and adaptation of the stimulation signals also may be manually controllable by patient, for example, when going to sleep or any other time when normal full device function is not needed or wanted by the patient.

Embodiments of the present invention also include a vestibular implant system having a power shifting mode wherein the vestibular stimulation signals are adapted to change over time to reduce patient discomfort while changing power operation of the system. The system may be operated in power shifting mode when starting up and/or when shutting down. Adaptation of the vestibular stimulation signals may include changing over time the pulse duration, pulse repetition rate, pulse train length, and/or signal amplitude. The system may further include one or more physiologic sensors that develop a physiologic signal reflecting a physiological condition of an implant patient. From that, adaptation of the vestibular stimulation signals may further be responsive to the physiological signal.

Implementation of power-saving modes (e.g., with constant pacing) upon low battery status to power down sensors and other components allows for a longer battery usage time at an acceptable price of having only constant pacing. Moreover, battery life tine and system safety should increase as soft onset/soft stop reduce the discomfort of system operating transitions and reduce the risk of injury by falls or accidents (e.g., if the system were to suddenly stop stimulating). Implementation of a power-saving mode with adaptive operation of the motion sensors (where the sensors are automatically de-activated when rotational and/or linear acceleration are below a certain threshold value) allows for a longer battery usage time virtually without notice by the patient and adds to an increased battery life time. This can be especially advantageous for situations where the patient is not exposed to motion/acceleration (e.g., while the patient is sleeping). When the implant switches into the power-saving mode, the patient may recognize this (if awake). The patient can then interpret this shift as an indication of a low-battery condition, in effect, an automatic notification to the patient of the need to recharge the battery.

In the foregoing, references to vestibular implant systems should be understood broadly to include all implantable arrangements that provide stimulation signals affecting the balance sensing system. Specifically such arrangements may or may not include motion sensors, whether internal or external. For example, a vestibular implant system without motion sensing signals may be useful for treatment related to Meniere's disease and may be thought of as a Meniere's implant. And vestibular implant arrangements may also be integrated together with other related implantable systems such as middle ear implants, cochlear implants, bone conduction implants, auditory brainstem implants, etc. And the stimulation signals may occur either by electrical means as commonly used in current cochlear implant technology, by optical means (e.g. as disclosed in U.S. Pat. No. 7,488,341 and in U.S. patent application Ser. No. 12/368,548; both incorporated herein by reference), by mechanical means (e.g. as disclosed in U.S. patent application Ser. No. 11/193,034, incorporated herein by reference), and or some combination of different types of stimulation signals.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A vestibular implant system comprising:
   an implantable vestibular stimulator providing vestibular stimulation signals to stimulate target neural tissue for vestibular sensation by a patient; and
   at least one motion sensor controllably powered by the vestibular implant system and developing a motion signal reflecting head motion of an implant patient;
   wherein the vestibular stimulator includes at least two different operating modes:
   i. a sensor controlled mode wherein the at least one motion sensor is powered and the vestibular stimulation signals are developed as a dependent function of the motion signal, and
   ii. a sensor independent mode wherein the at least one motion sensor is unpowered and the vestibular stimulation signals, if any, are developed independently of the motion signal; and
   wherein the vestibular stimulation signals include soft-start switch-on and soft-off power down characteristics in which the vestibular stimulation signals gradually transition over a given period of time.

2. A vestibular implant system according to claim 1, further comprising:
   at least one mode control sensor separate and independent from the at least one motion sensor and developing a mode control signal reflecting head motion of the implant patient, wherein the vestibular stimulator system shifts to sensor independent mode when then mode control signal falls below a threshold value.

3. A vestibular implant system according to claim 2, wherein the system shifts to sensor controlled mode when the mode control signal exceeds the threshold value.

4. A vestibular implant system according to claim 1, wherein the vestibular stimulator system shifts to sensor independent mode when the motion signal falls below a threshold value.

5. A vestibular implant system according to claim 4, wherein the system shifts to sensor controlled mode when the motion signal exceeds the threshold value.

6. A vestibular implant system according to claim 1, wherein the vestibular stimulation signal is a constant pacing signal in sensor independent mode.

7. A vestibular implant system according to claim 1, wherein no vestibular stimulation signal is developed in sensor independent mode.

8. A vestibular implant system according to claim 1, wherein the system shifts operating modes as a function of time of day.

9. A vestibular implant system according to claim 1, wherein the system shifts to sensor independent mode in response to a system malfunction.

10. A vestibular implant system according to claim 1, wherein the sensor independent mode includes a patient sleep mode and wherein the vestibular stimulation signals are adapted to promote sleep of the patient.

11. A vestibular implant system according to claim 1, wherein the system shifts operating modes as a function of system power status.

12. A vestibular implant system comprising:
an implantable vestibular stimulator providing vestibular stimulation signals to stimulate target neural tissue for vestibular sensation by a patient; and
at least one motion sensor developing a motion signal reflecting head motion of an implant patient;
wherein the vestibular stimulator includes at least two different operating modes:
  i. a sensor controlled mode wherein the vestibular stimulation signals are developed as a dependent function of the motion signal, and
  ii. a power shifting mode wherein the vestibular stimulation signal is adapted to change over time to reduce patient discomfort while changing power operation of the system; and
wherein the vestibular stimulation signals include soft-start switch-on and soft-off power down characteristics in which the vestibular stimulation signals gradually transition over a given period of time.

13. A vestibular implant system according to claim 12, wherein the system is operated in power shifting mode when starting up.

14. A vestibular implant system according to claim 12, wherein the system is operated in power shifting mode when shutting down.

15. A vestibular implant system according to claim 12, wherein adaptation of the vestibular stimulation signal includes changing pulse duration over time.

16. A vestibular implant system according to claim 12, wherein adaptation of the vestibular stimulation signal includes changing pulse repetition rate over time.

17. A vestibular implant system according to claim 12, wherein adaptation of the vestibular stimulation signal includes changing pulse train length over time.

18. A vestibular implant system according to claim 12, wherein adaptation of the vestibular stimulation signal includes changing signal amplitude over time.

19. A vestibular implant system according to claim 12, further comprising:
at least one physiologic sensor developing a physiologic signal reflecting a physiological condition of an implant patient; and
wherein adaptation of the vestibular stimulation signals further is responsive to the physiological signal.

* * * * *

UNITED STATES PATENT AND TRADEMARK OFFICE
CERTIFICATE OF CORRECTION

PATENT NO. : 8,751,012 B2    Page 1 of 1
APPLICATION NO. : 13/743513
DATED : June 10, 2014
INVENTOR(S) : Jäger et al.

It is certified that error appears in the above-identified patent and that said Letters Patent is hereby corrected as shown below:

On title page, item [73],
replace "MED-EL Elektromedizinische Geraete GmbH, Innsbruck (AT)"
with --MED-EL Elektromedizinische Geraete GmbH, Innsbruck (AT) and
The Johns Hopkins University, Baltimore, MD (US)--

Signed and Sealed this
Twenty-third Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,751,012 B2
APPLICATION NO. : 13/743513
DATED : June 10, 2014
INVENTOR(S) : Andreas Jäger et al.

It is certified that error appears in the above-identified patent and that said Letters Patent is hereby corrected as shown below:

In the Specification

Column 1, Line 9, please insert:
--This invention was made with government support under DC009255, awarded by the National Institutes of Health. The government has certain rights in the invention.--

Signed and Sealed this
Twenty-fifth Day of August, 2020

Andrei Iancu
*Director of the United States Patent and Trademark Office*